US 6,539,156 B1

(12) United States Patent
Dickson et al.

(10) Patent No.: US 6,539,156 B1
(45) Date of Patent: Mar. 25, 2003

(54) APPARATUS AND METHOD OF OPTICAL TRANSFER AND CONTROL IN PLASMON SUPPORTING METAL NANOSTRUCTURES

(75) Inventors: Robert M. Dickson, Atlanta, GA (US); Louis A. Lyon, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 180 days.

(21) Appl. No.: 09/704,931

(22) Filed: Nov. 2, 2000

Related U.S. Application Data
(60) Provisional application No. 60/220,920, filed on Jul. 26, 2000, provisional application No. 60/205,958, filed on May 19, 2000, and provisional application No. 60/163,025, filed on Nov. 2, 1999.

(51) Int. Cl.[7] .............................................. G02B 6/10
(52) U.S. Cl. ....................................... 385/129; 385/141
(58) Field of Search ............................... 385/129, 130, 385/131, 141, 14

(56) References Cited

U.S. PATENT DOCUMENTS 5,442,448 A * 8/1995 Knoll .......................... 356/445
6,236,033 B1 * 5/2001 Ebbesen et al. ............ 250/216

OTHER PUBLICATIONS

T. Greber, J. Osterwalder, S. Hüffner, and L. Schlapbach; Enhanced Plasmon–Loss Emission Along Al[011] Chains Upon Heating; Oct. 15, 1991; pp. 8958–8961.

P. Dawson, F. de Fornel, and J.P. Goudonnet; Imaging of Surface Plasmon Propagation and Edge Interaction Using a Phonton Scanning Tunneling Microscope; May 2, 1994; pp. 2927–2930.

P. Dawson, K.W. Smith, F. de Fornel, J.P. Goudonnet; Imaging of Surface Plasmon Launch and Propagation Using a Photon Scanning Tunneling Microscope; Nov./Dec. 1993; pp. 287–292.

B. Hecht, H. Bielefeldt, L. Novotny, Y. Inouye, and D.W. Pohl; Local Excitation, Scattering, and Interference of Surface Plasmons; Aug. 26, 1996; pp. 1889–1892.

J.R. Krenn, A. Dereux, J.C. Weeber, E. Bourillot, Y. Lacroute, and J.P. Goudonnet; Squeezing the Optical Near–Field Zone by Plasmon Coupling of Metallic Nanoparticles; Mar. 22, 1999; pp. 2590–2593.

Jean–Claude Weeber; Cristian Girard; Joachim R. Krenn, Alain Dereux, and Jean–Pierre Goudonnet; Near–Field Optical Properties of Localized Plasmons Around Lithographically Designed Nanostructures; Sep. 1, 1999; pp. 2576–2583.

Jean–Claude Weeber; Alain Dereux; Christian Girard; Joachim R. Krenn and Jean–Pierre Goudonnet; Plasmon Polaritions of Metallic Nanowires For Controlling Submicron Propagation of Light; Sep. 15, 1999; pp. 9061–9068.

Robert M. Dickson and L. Andrew Lyon; Unidirectional Plasmon Propagation in Metallic Nanowires; Apr. 14, 2000; pp. 6095–6098.

Weeber et al., Plasmon Polaritons of Metallic Nanowires for Controlling Submicron Propagation of Light; Sep. 19, 1999; pp. 9061–9068.*

* cited by examiner

Primary Examiner—Robert H. Kim
Assistant Examiner—Chih-Cheng G. Kao
(74) Attorney, Agent, or Firm—Scott A. Horstemeyer; Thomas, Kayden, Horstemeyer & Risley, LLP

(57) ABSTRACT

An apparatus and method are provided for converting light into a surface plasmon polariton on a plasmon supporting nanostructure and then controlling the emission of the re-emitting light. A circuit component is also described that is constructed of a nanostructure, which is comprised of at least one plasmon supporting metal. The metal can propagate the light, as a surface plasmon polariton, through the one-dimensional nanostructure and re-emit the light. The metal is a plasmon supporting metal, for example but not limited to, gold, silver, copper, and aluminum.

32 Claims, 4 Drawing Sheets

APPARATUS AND METHOD OF OPTICAL TRANSFER AND CONTROL IN PLASMON SUPPORTING METAL NANOSTRUCTURES

CROSS-REFERENCE TO RELATED APPLICATIONS

This application is related and claims priority to copending U.S provisional patent applications: "OPTICAL TRANSFER AND DATA FLOW CONTROL IN METAL NANOSTRUCTURES VIA PLASMON PROPOGATION MODULATION" filed on Nov. 2, 1999 and accorded serial No. 60/163,025; "NANOSCALE DEVICES FOR OPTICAL COMPUTING" filed on May 19, 2000 and accorded serial No. 60/205,958, "NANOSCALE WAVE GUIDES AND OPTOELECTRONICS" filed on Jul. 26, 2000 and accorded Ser. No. 60/220,920. All of the foregoing copending U.S. provisional patent applications are entirely incorporated herein by reference.

TECHNICAL FIELD

The present invention is generally related to plasmon supporting nanostructures that are used in circuit components and, more particularly, is related to an apparatus and method of converting light into surface plasmon polaritons upon a plasmon supporting metallic one dimensional nanostructure and then re-emitting another light.

BACKGROUND OF THE INVENTION

Scientists have been studying molecular electronics in an effort to circumvent the size limitations on electronic components. This has been done in part because molecular electronics has increased flexibility and ease of processing with extremely high density information processing. Although some niche applications have been found for such materials, many problems such as robustness, processability, stability, and addressability still exist. While smaller is very often better, such devices have limited bandwidth due to the capacitance of electronic circuits. Conversely, optical information processing holds promise for significantly higher bandwidth devices, but suffers from even more severe size and addressability concerns than those that limit conventional electronics. These problems result from the diffraction limit—the spatial extent of light in a medium of refractive index n is limited by diffraction to about $\lambda/2n$, where $\lambda$ is the free space wavelength of light. Thus, although the construction of conventional waveguides from high index materials enables the minimum beam size to be decreased significantly, waveguides are typically several times this diameter to adequately confine light via total internal reflection (TIR). Both modern lithography methods and molecular electronics have demonstrated success at alleviating this size constraint for purely electronic devices, but diffraction imposes a fundamental size limit in further shrinking devices for optical information processing.

The ability to transport optical signals through structures that are smaller than the free-space optical wavelength relies upon one of two physical processes taking place. One technique is for a waveguide to be constructed of an extremely high refractive index material. This technique can be accomplished in a simple fashion by using high index glasses to form optical fibers, but even the highest indices (n is about 3) shrink the limiting dimensions to $\lambda/6$, or about 100 nm for visible light. Since the range of angles capable of propagating in such fibers is smaller than that in a tightly focused spot, realistic visible waveguide dimensions of about 400 nm should be attainable. Thus, while optical fibers are nearly ideal for low loss, long range optical communication, the size constraints imposed by diffraction limits their incorporation into future nanoscale optical devices.

Alternatively, 30 nm diameter metallic structures have been theoretically proposed to confine and transmit light due to the large negative dielectric constants. Because light in such materials has imaginary transverse wave vectors, the minimum waveguide diameter can be made arbitrarily small. However, as such structures shrink, the metallic structures exhibit exponentially increasing losses due to both the negative (absorptive) and imaginary (imperfectly conductive) portions of the dielectric constant. Since the optical dielectric constant, $\epsilon$, is the square of the complex refractive index, and large negative dielectric constants result from the large imaginary refractive index of the material, light propagating in such devices will be strongly attenuated because of absorption, rendering them impractical for device fabrication.

Thus, a heretofore unaddressed need exists in the industry to address the aforementioned deficiencies and inadequacies.

SUMMARY OF THE INVENTION

The present invention provides an apparatus and method for converting light into a surface plasmon polariton on a plasmon supporting nanostructure and then re-emitting light.

An exemplary embodiment of the present invention is a circuit component constructed of a nanostructure, which has at least one plasmon supporting metal. The metal can propagate the light, as a surface plasmon polariton, through the nanostructure and re-emit the light. The light is propagated through the nanostructure using a one-dimensional nanostructure-confined surface plasmon. The nanostructure can be, but is not limited to, one-dimensional or pseudo one-dimensional (hereinafter one-dimensional). The metal is a plasmon supporting metal, e.g. gold, silver, copper, and aluminum.

The present invention can also be viewed as providing one or more methods for converting light into a surface plasmon polariton on a plasmon supporting nanostructure and then re-emitting light. In this regard, one such method can be broadly summarized by the following steps: providing a nanostructure; directing a first light into the nanostructure, wherein said first light has a first light energy; converting the first light energy into an surface plasmon polariton; transporting the surface plasmon polariton through the nanostructure; converting the surface plasmon polariton into a second light. In another embodiment of the present invention, a step can be added for controlling the surface plasmon polariton propagation through the nanostructure.

In addition, the present invention can be viewed as one or more apparatuses for converting light into a surface plasmon polariton on a plasmon supporting nanostructure and then re-emitting light. The apparatus has a means for converting light energy into a surface plasmon polariton. Further, the apparatus has a means for transporting the surface plasmon polariton through the nanostructure. Furthermore, the apparatus has a means for converting the surface plasmon polariton back into light. In an alternative embodiment, the apparatus has a means for controlling the surface plasmon polariton propagation through the nanostructure.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

As discussed above, the ability to transport optical signals through structures that are smaller than the free-space optical wavelength relies upon one of two physical processes taking place. The second process, not discussed above, is to convert the light, photons, into electromagnetic modes that are confined by different spatial boundary conditions than those imposed upon light. In other words, the optical energy of the light is converted into a surface plasmon polariton transported via plasmon propagation. The current embodiments of the following invention are based on this premise.

Although optical energy usually propagates through materials as light, in free electron metals (films or nanoparticles) light can be efficiently converted into surface plasmons at optical frequencies via the metal's large negative dielectric constant. A plasmon is a surface-bound electromagnetic wave resulting from the collective oscillation of the free electrons within the metal. These modes are typically excited with specific angles, wavelengths, and therefore momenta of the incident light (photons). This effectively amounts to light absorption by the free electron gas that excites a propagating electromagnetic wave within the metal. Energy propagation proceeds in the direction of the wave vector until the plasmon mode decays from either collisional lattice damping, or re-emission at a scattering center/discontinuity in the metal surface as an elastically scattered photon. Not subject to the same size and attenuation limitations resulting from nanoscale light propagation, surface plasmons of a given frequency have significantly higher momenta than does light either in free space or in a medium of the same dielectric. This difference in momentum from collective electron excitation versus light propagation is what confines the electromagnetic energy to the free electron metal.

When a scattering center/discontinuity in the metal film is reached the energy couples back out to free-space as light. By utilizing the surface plasmon mode of a free electron metal as a conduit for optical energy transport, the conduit may be reduced to a size fundamentally limited by a combination of the Thomas-Fermi screening length (e.g. about 0.1 nm in Au) and the electron mean free path (e.g. about 4 nm in Au), just as in electronic components. These dimensional limits are orders of magnitude smaller than those mediating light confinement in high index materials, yet still enable both electronic and optical (plasmonic) information transfer, simultaneously.

Figure 1:
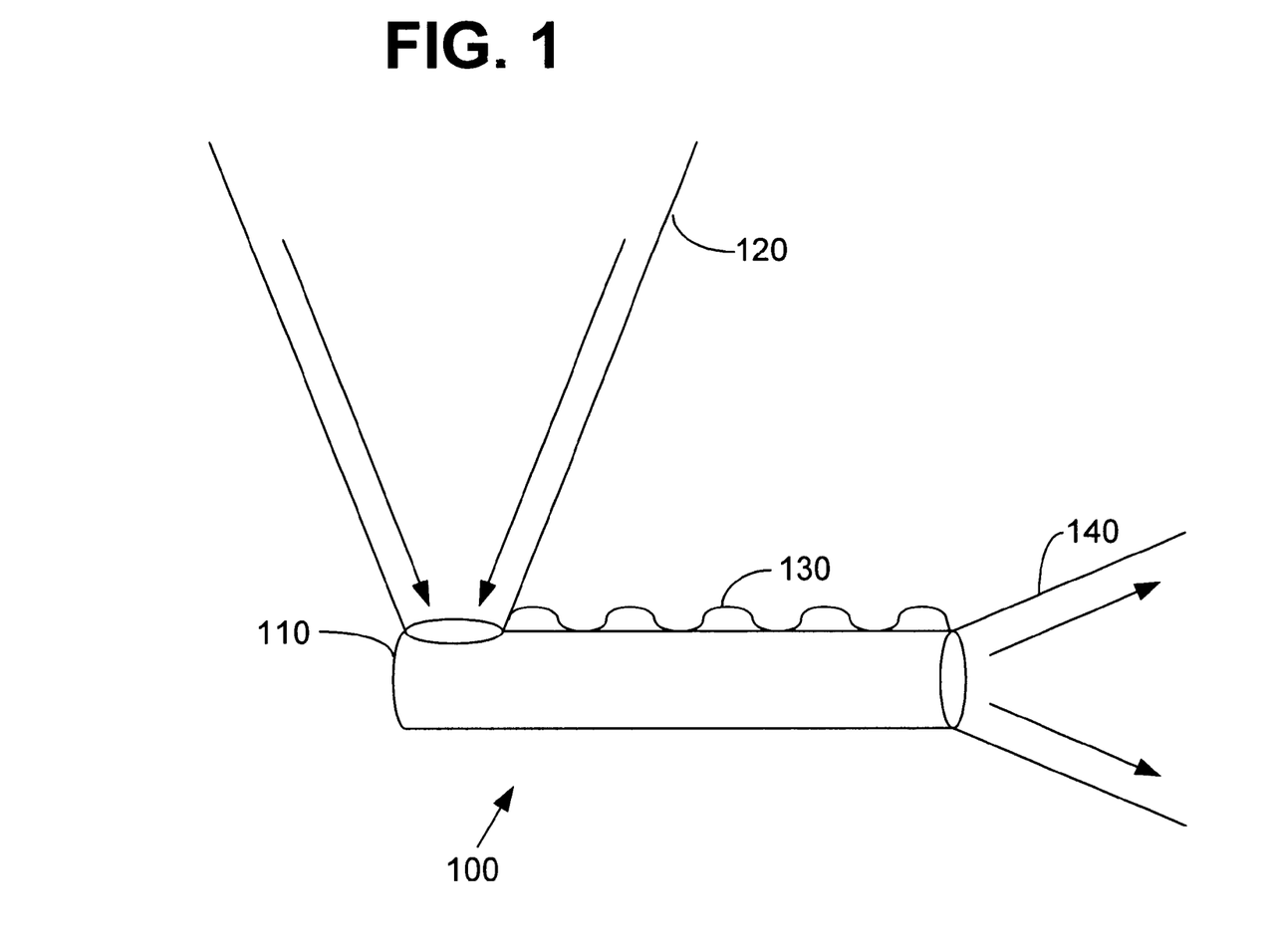
FIG. 1 illustrates a nanostructure in accordance with the present invention.

A preferred embodiment of the present invention is a circuit component, as shown in FIG. 1. The circuit component 100 includes a nanostructure 110 (hereinafter one-dimensional nanostructure), that upon illumination can convert optical energy 120 into a surface plasmon polariton which transfers the surface plasmon polariton down the length of the nanostructure 110 using a one-dimensional nanostructure-confined surface plasmon 130. After the surface plasmon polariton traverses the length of the nanostructure 110, the surface plasmon polariton is converted back into optical energy 140 and emitted as a light that is characteristic of the incident light. The nanostructure can be, but is not limited to, a one-dimensional or pseudo one-dimensional nanostructure. The propagation behavior is a function of the nanostructure 110 length, diameter, composition, excitation wavelength, incident polarization, and surface roughness. In addition, propagation altering materials or coatings such as biological components, chemical components, or nanoparticles can be placed on the nanostructure 110 surface to alter the emission.

Some nonlimiting examples of chemical components include, but are not limited to, organic coatings, polymer coatings, hydrogels, conducting polymers, alkanethiols, aryl-thiols, alkylamines, arylamines, polyimides, polystyrenes, polyacrylates, polyacrylamides, and polyelectrolytes. Biological components can be used to analyze biological interactions and these include, but are not limited to, protein-protein, protein-ligand, protein-DNA, DNA-DNA, protein-RNA, protein-lipid, etc. The biological components can be wild-type (or native) structures, mutated structures, biosynthetic biomolecules, synthetically designed mimics, or any combination thereof. Additionally, the biological components may also be labeled with molecular or particulate structures (e.g., metal nanoparticles, polymer nanoparticles, semiconductor nanoparticles, fluorescent labels, radiolabels, liposomes, vesicles, glass particles, etc.) or combinations thereof. In addition, the nanostructure 110 segments can be composed of non-plasmon supporting metals, semiconductors, polymers, or insulating materials, provided the nanostructure is composed of enough of a plasmon-supporting metal to produce the desired results. Further details concerning surface plasmon polaritons and one-dimensional nanostructure-confined surface plasmons will be discussed below. The circuit component 100 is an electrical circuit, optical circuit, or combination thereof. More specifically, the circuit component includes, but is not limited to, a unidirectional conduit, diode, transistor, amplifier, switch, filter, optical gate and combinations thereof. The nanostructure 110 can be of various shapes, which include, but are not limited to, nanostructures 110 with well-defined curvature, nanostructures 110 with tapered interconnects, as well as others. The nanostructure 110 is made of at least one plasmon supporting metal. The plasmon supporting metals include, but are not limited to, gold (Au), silver (Ag), copper (Cu), and aluminum (Al). The nanostructures 110 dimensions can range in diameter from approximately 5 nm to approximately $\lambda/4$ (about 100 nm for visible light) and in length from approximately 1 micron to more than 100 microns in length.

An alternative embodiment of the present invention is the method of converting light into a surface plasmon polariton and then converting it back into light, i.e. photons. The first step of this method involves providing a one-dimensional nanostructure 110 with two ends. The nanostructure is similar to the type described above. Next, a light source is directed onto the first end of the nanostructure 110. The light source has a particular optical energy. The optical energy is converted into a surface plasmon polariton upon the nanostructure 110 surface. The surface plasmon polariton is transferred from the first end of the nanostructure 110 to the second end of the nanostructure 110 using a one-dimensional surface-confined plasmon. Then the surface plasmon polariton is converted back into a light upon reaching the second end of the nanostructure 110. In addition, an alternative embodiment allows for a step of controlling the propagation of the surface plasmon polariton through the surface before the light is emitted. This can be done with biologically components, chemical components, or nanoparticles.

A further embodiment of the present invention is an apparatus for converting light into a surface plasmon polariton and then converting it back into light. The apparatus can have a means for providing a one-dimensional nanostructure 110 with two ends. The nanostructure 110 is similar to the type described above. In addition the apparatus can have a means for directing a light source onto the first end of the nanostructure 110. The light source or photons have a particular optical energy. Additionally, the apparatus has a means for converting the optical energy into a surface plasmon polariton upon the nanostructure 110 surface. Further, the apparatus has a means for transferring the surface plasmon polariton from the first end of the nanostructure 110 to the second end of the nanostructure 110 using a one-dimensional surface-confined plasmon. Furthermore, the apparatus has a means for converting the surface plasmon polariton back into light upon reaching the second end of the photon. In addition, an alternative embodiment of the apparatus has a means for controlling the propagation of the surface plasmon polariton through the surface before it is emitted. This can be done with biologically components, chemical components, or nanoparticles.

Plasmon propagation is not limited by light absorption resulting from the imaginary component of the refractive index, but is mainly limited by the lack of perfect electron mobility. Since plasmons propagate at velocities approaching the speed of light with extremely high bandwidths, and the dimensions governing plasmon behavior are much smaller than the diffraction limit, controlling plasmon propagation in reduced dimension structures promises great advances in high density optical information processing. Plasmon propagation over hundreds of microns in nanometer-scale devices should be readily allowed, thereby enabling orders of magnitude increases in bandwidth without significant size limitations. Propagation length limitations can be circumvented through plasmon amplification, a process analogous to that in optical fiber communications. Furthermore, most of the structures described below are attainable with commercial lithography techniques; thus, the economic barriers to the production of plasmon-based devices will be significantly lower than those associated with many other proposed optical computing architectures.

A surface plasmon exhibits two components, a propagating surface-bound wave parallel to the film surface and a non-propagating evanescent field decaying exponentially with distance perpendicular to the interface. The surface-bound mode has a real wavevector that is parallel to the direction of energy transport. The evanescent field perpendicular to the metal nanostructure 110 surface, however, is, by definition, a non-propagating, loss-less mode, that with an exponential decay constant of about $\lambda/2$, extends but does not propagate into the surrounding dielectric. Interactions of this evanescent field with the material surrounding the nanostructure 110 is what enables detection of chemical and biological components, as it alters plasmon transmission along the length of the nanostructure 110.

Surface plasmon polaritons are confined to within a few nanometers of the surface, perpendicular to their direction of propagation. Because, upon absorbing light, thin metals, e.g., nanostructures 110, convert optical energy into propagating surface plasmon polaritons, the plasmon-mediated transmission of electromagnetic energy is neither limited by the absorptive processes nor the confinement issues restricting light propagation through nanostructured 110 materials. By utilizing plasmon supporting metal nanostructures 110, one-dimensional nanostructure-confined plasmon conduits (e.g. circuit components) can be constructed with dimensions that are orders of magnitude smaller than the diffraction limit, yet still readily transport electromagnetic energy at optical frequencies. Plasmon supporting metal nanostructures 110 can be readily prepared utilizing plating solutions and structures of approximately 20 nm diameter and up to approximately 40 microns in length can be grown electrochemically. Generally, plasmon supporting metals are used to construct the nanostructures 110. These include, but are not limited to, gold, silver, copper, aluminum, or combinations or alloys thereof. In addition, multimetal nanostructures 110 can also be grown. One nonexclusive method for performing this to simply change the plating solution during growth to produce a nanostructure 110 composed with one or more plasmon supporting metals. These one-dimensional nanostructures 110 can propagate surface plasmon polaritons with sub-diffraction limited dimensions.

A. The following describes a non-limiting illustrative example of a preferred embodiment of this invention that uses gold (Au) and silver (Ag) to create circuit components that can convert light into a surface plasmon polariton, transfer the surface plasmon polariton, convert the surface plasmon polariton back into light by emitting light. Plasmon coupling and propagation in both Au and Ag can be modulated by changing the light energy. Despite the fact that both Au and Ag display free-electron behavior, their wavelength-dependent optical properties differ, as is evidenced by their disparate plasmon decays with distance, I(x):

$$I(x) = \exp(-2k_x'' x) \qquad \text{(Equation 1a)}$$

in which the imaginary portion of the plasmon momentum wave vector is as follows:

$$k_x'' = \frac{\omega}{c} \left( \frac{\varepsilon_1' \varepsilon_2}{\varepsilon_1' + \varepsilon_2} \right)^{\frac{3}{2}} \frac{\varepsilon_1''}{2(\varepsilon_1')^2}. \qquad \text{(Equation 1b)}$$

In Equation 1b, $\omega$ is the optical excitation frequency, c is the speed of light, $\varepsilon_1'$ and $\varepsilon_2$ are the real dielectric function of the metal and of the surrounding medium, respectively, and $\varepsilon_1''$ is the imaginary part of the metal dielectric function. The plasmon propagation length is quite long when either metal is illuminated at 820 nm, but is significant for Ag at 532 nm. In other words, Ag behaves as a free electron metal at both 532 nm and 820 nm, while Au behaves ideally at 820 nm. Using equations 1, one can readily calculate that plasmon propagation lengths in Ag are about 30 $\mu$m at 532 nm, and about 500 $\mu$m in the near infrared.

Plasmon conduits from high aspect-ratio metal nanostructures 110 have been made. Generally, high aspect ratio is greater than 3:1, length:width. These nanostructures 110 are solid nanoparticles, approximately 20 nm in diameter and many microns in length. The nanostructures 110 are generally cylindrical but can also be any other appropriate shape. The nanostructures 110 of the preferred embodiment have been made of Au, Ag, or a combination thereof.

As shown in FIG. 1 and discussed above, when plasmon propagation is initiated parallel to the long axis of the nanostructure 110, the incident light passes down the length of the nanostructure 110 as a surface plasmon polariton, and then re-emerge from the end as light that is characteristic of the incident light (via plasmon scattering). The nanostructures 110 scatter light in a manner characteristic of their interactions with the incident beam. Although light couples into the nanostructure 110 at all points along its long axis, coupling efficiency should be highest at the segment first interacting with the laser due to its high curvature. Under 532-nm illumination, the Au nanostructure scatters light from the input segment. Conversely, the Ag nanostructure displays strong emission at both the input and output segments. Upon illumination at 820 nm, however, both the Au and Ag nanostructure display emission patterns that are similar to Ag at 532 nm; light emanates from both the input and output segments of the nanostructure. Contrary to expectations for ordinary light scattering (where scattering intensity should increase at shorter wavelengths), this wavelength dependence strongly suggests plasmon propagation along the nanostructure axis with subsequent emission at the discontinuous distal output segment.

Plasmon excitation can occur from any section of the nanostructure 110. Therefore, the illumination should be directed onto the input segment of the nanostructure 110. When the input segment of a Au nanostructure is illuminated at 532 nm, the nanostructure appears completely dark and scatters at the input segment. However, when Ag is illuminated under the same conditions, emission is observed from the output segment. The emission can be many microns away from the illumination point. At 820 nm, however, light propagates through and out of the distal output segments of both nanostructures, demonstrating that both excitation of surface plasmon modes and re-emission at the nanostructure output are at least partly dependent on the metal optical properties. These results even more clearly demonstrate that the observed behavior results from plasmon coupling into, propagation through, and emission from the nanostructures.

B. The following is another non-limiting illustrative example of a preferred embodiment of the present invention that demonstrates a nanostructure 110 diode or more generally a unidirectional conduit. In addition to the one-dimensional wavelength-dependent plasmon-mediated light propagation, Au is seen to limit the plasmon propagation length more than Ag, even at 820 nm. Therefore, the wavelength and metal dependence of plasmon propagation can be used to control the direction of energy flow within a single conduit. Through construction of a Au/Ag nanostructure in two discrete segments, a electro-optic heterojunction, or diode, has been constructed. As with the monolithic nanostructures described above, these segmented devices can be produced via a template-directed electrosynthetic technique. Generally, nanostructures of a specific length are grown from the Au plating solution, followed by replacement of that solution with a Ag solution. Continued electroplating from the new medium results in a second nanostructure segment composed of Ag. The bimetallic nanostructure is a single entity with a well-defined heterojunction as opposed to two separate nanoparticles in close proximity.

Figure 2A:
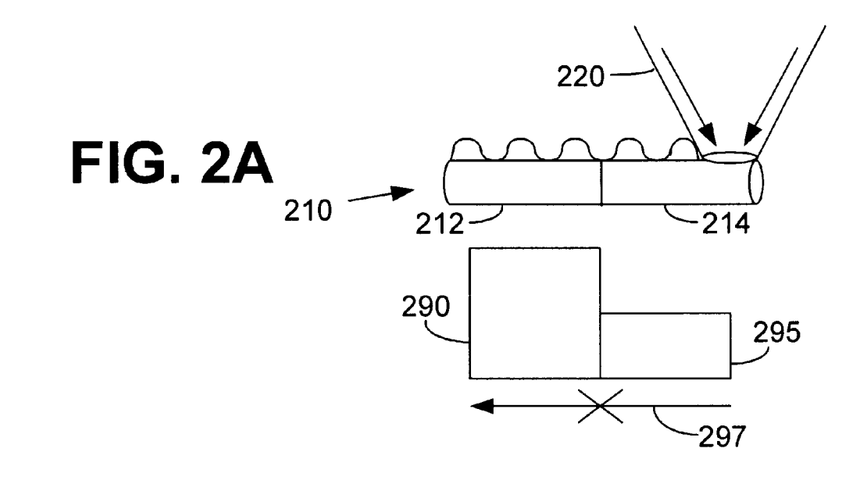
FIGS. 2A and 2B illustrate a nanostructure similar to the one illustrated in FIG. 1 except that the nanostructure is a bimetallic nanostructure.
Figure 2B:
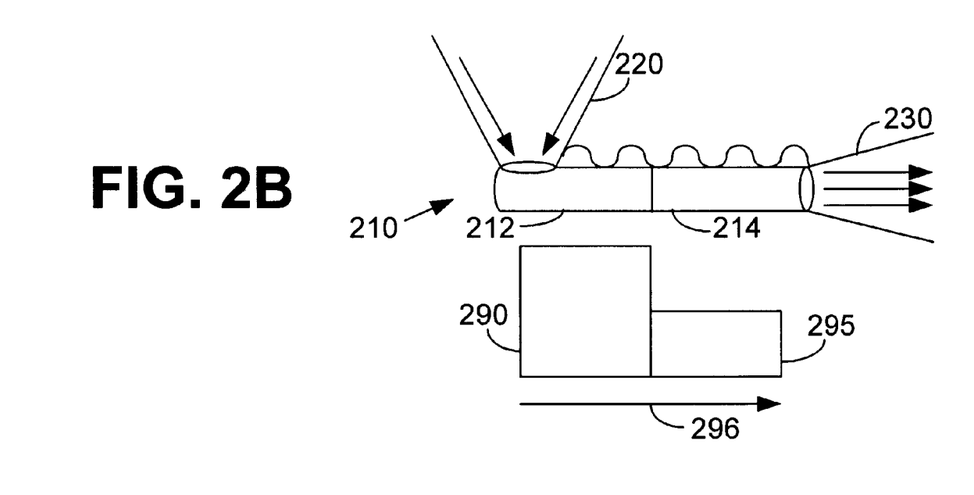

Since Au does not support plasmon propagation at 532 nm, plasmons will propagate through the bimetallic nanostructure at 820 nm. FIGS. 2A and 2B show a bimetallic nanostructure 210 that is composed of two segments. The first segment 212 is Au, while the second segment 214 is Ag. In FIG. 2A the incident light 220 is directed at the Ag segment 214 and there is no resulting light emanating from the Au segment 212. This demonstrates that the optical energy is not transferred down the nanostructure from the silver segment 214 to the Au segment 212. In contrast, light emission is clearly observable from the Ag end of the nanostructure when the Au segment is illuminated at 820 nm. This demonstrates that the optical energy of the light is converted into a surface plasmon polariton and transferred to the silver segment 214. The plasmon mode excited at 820 nm 220 is able to couple from the Au portion 212 into the Ag portion 214 with high efficiency, and then re-emit 230 as it scatters at the end of the Ag segment 214. The plasmons propagate much farther in Ag 214 than in Au 212, which enables efficient plasmon propagation in the direction from Au 212 to Ag 214. However, in the opposite direction propagation from Ag 214 to Au 212 sees a much steeper potential wall, allowing less light to couple through to the Au segment 212. In fact, due to the different propagation lengths in the two metals, if the same nanostructure is excited at 820 nm via the Ag segment 214, no light is emitted from the Au segment 212.

The directionality of reflection at the Ag/Au boundary is qualitatively reproduced and understood by employing a simple two level potential barrier model, as shown in FIGS. 2A and 2B. In these figures, the Au possesses a high potential 290 and the Ag has a lower but nonzero potential 295; the light has energy slightly lower than either metallic potential. Under these conditions, the probability decays exponentially in each metal, but more rapidly in Au (mimicking the actual plasmon decays). A significant directionality in the reflection and transmission coefficients at the interface results. As shown in FIG. 2B, when energy passes from the high potential region, Au, to the low potential region, Ag, the reflection coefficient is quite low 296. Conversely, as shown in FIG. 2A, passage from a low potential region to a high potential region produces a highly reflective interface 297. Thus, by controlling nanostructure composition, a directional propagation of the surface plasmon polariton conduit can be constructed, e.g., a simple nanoscale opto-electronic diode.

With much higher bandwidths than similarly sized electronic devices, the control of plasmons in such nanostructure unidirectional conduits or circuit components is significant for the future development of high-density optical information processing and sensing methods. Converting light into surface plasmons on plasmon supporting nanostructures demonstrates long-range, sub-diffraction light propagation. This is the first demonstration of long range optical energy transport in nanometer-scale structures via surface plasmons (or by any other method). Through control of nanostructure composition, not only can high density optical information transfer be achieved, but also control of information transfer and therefore optical processing has been demonstrated by utilizing the directional properties of a Au/Ag heterojunction. Optically encoded information can be initiated and the flow controlled with nanometer-scale accuracy over distances of many microns.

Figure 3A:
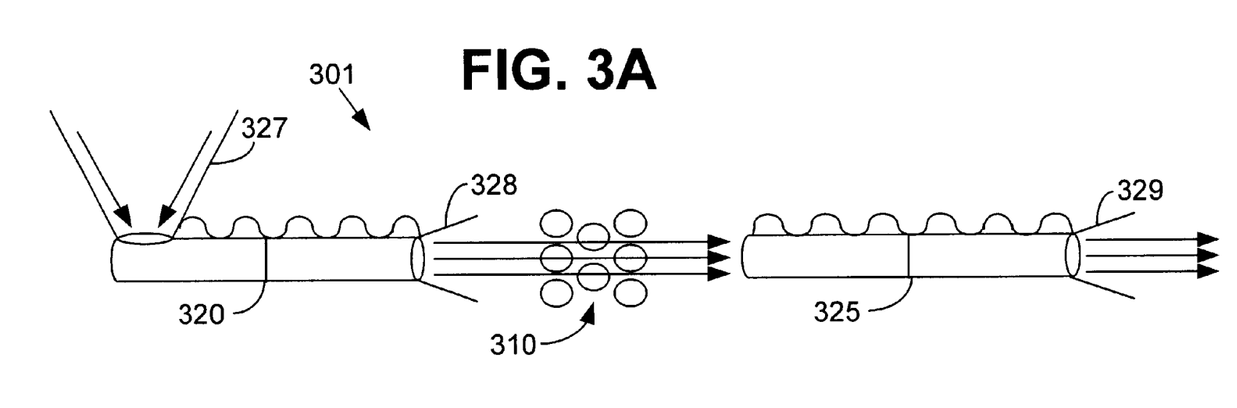
FIGS. 3A and 3B illustrates two pairs of nanostructures, similar to the one illustrated in FIG. 1, that have nanoparticles placed between each set of pairs.
Figure 3B:
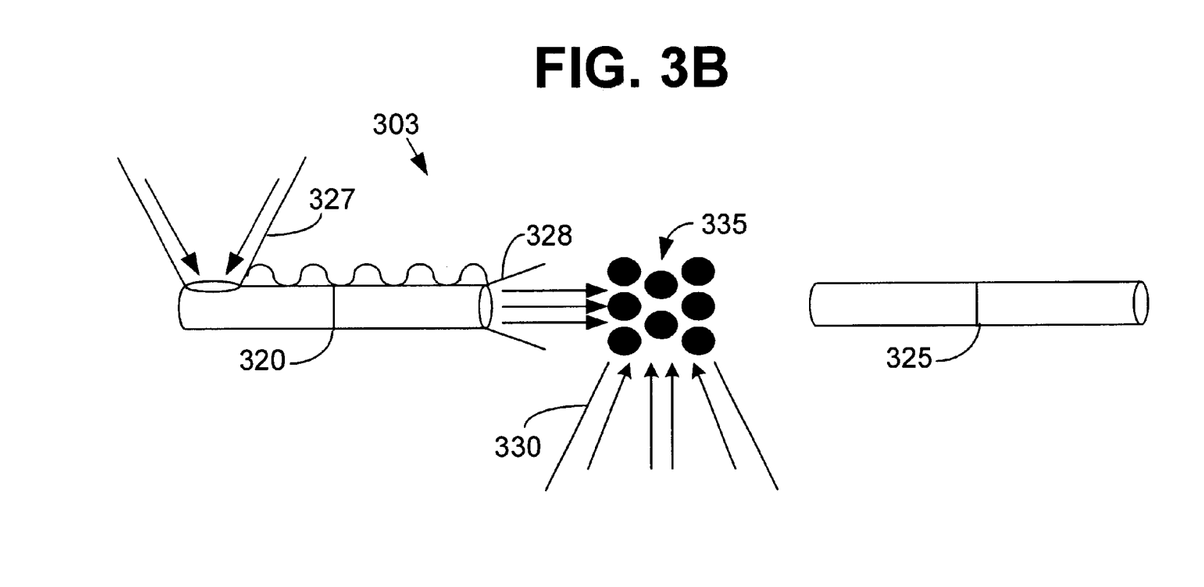

C. The following is another illustrative nonlimiting example of a preferred embodiment of the present invention that describes a transistor, as shown in FIGS. 3A and 3B. Generally, while electrical control of semiconductor doping is the current standard for transistor design, the control of plasmon propagation lengths is usually accomplished by modulation of the dielectric constant at the metal surface. This is the premise upon which surface plasmon resonance sensing is based. Modulation of the local dielectric function changes the resonance condition and hence the optimal wavelength or coupling angle and this approach will be used to construct nanostructure transistors. It is insufficient in terms of device speed and robustness to imagine controlling the dielectric through chemical adsorption/desorption reactions at the surface. Furthermore, the speed of optical computing is compromised if electrical switching is used. Accordingly, optical switching based on bandgap excitation of nanoparticles can be exploited to create optical gates for plasmon propagation.

The optical properties of some semiconductor nanoparticles 310 (e.g. $TiO_2$, ZnO, CdS, CdSe, ZnS, ZnSe, CdTe,) can be modulated significantly when electrons are promoted to the conduction band. When the plasmon excitation wavelength is resonant with an electronic transition of the semiconductor conduction band electrons, absorptive modulation of the plasmon propagation should result, which is also operative in a near-field coupling scheme. The efficiency of light transfer, e.g., data transfer, can be strongly modulated by the dielectric properties of the intervening medium; placement of nanoparticles 310 between two or more nanostructures will allow for modulation of through-space coupling.

An example of this is shown in FIGS. 3A and 3B. Introduction of particular semiconductor nanoparticles 310, for example about 5 nm diameter $TiO_2$ nanoparticles, to a spatially isolated region on or between two or more nanostructures 320 and 325 illuminated 327, followed by band-gap excitation with a particular frequency of light 330, e.g. about 380 nm light, will produce a structure that can be switched between a plasmon transmissive (380 nm off) 301 and absorptive (380 nm on) 303 state. FIG. 3A describes a structure 301 where the band-gap excitation is off. Light 327 is directed onto a first nanostructure 320 and the light 328 is re-emitted at the distal end of the first nanostructure 320. The light 328 is not absorbed by the semiconductor particles 310 and travel into the second nanostructure 325, which subsequently re-emits the light 329. However, in FIG. 3B the re-emitted light 328 is absorbed by the activated, band-gap excitation 330, semiconductor particles 335, and no light reaches the second nanostructure 325.

This will result in a nanostructure transistor-type 301 and 303 device that can be switched at rates comparable to optical switching schemes. Furthermore, the nanostructure 301 and 303 can be a wavelength specific data filter; plasmons excited at frequencies that are not resonant with the semiconductor nanoparticles gate will not be switched while resonant plasmons will not pass the gate. The signal modulation can be controlled by various means, such as, but not limited to, controlling the coverage of particles, the particle size, doping, and attachment chemistry (linker length).

Coupling nanostructures 110 (coupling of circuit components) will be done to create larger and more complex circuits. The simplest case would involve the coupling of energy emitted from the tip of one nanostructure 320 into the end of another nanostructure 325, as shown in FIGS. 3A and 3B. Efficient coupling of the two nanostructures 320 and 325 will depend on a number of factors, including, but not limited to, tip-to-tip distance, tip curvature, orientation of the nanostructures with respect to the propagation wavevector, nanostructure diameter and width, and nanostructure composition.

D. Nanostructure filters can be created by altering the propagation characteristics of the nanostructure. It is well established that alloys of two plasmon-carrying metals exhibit plasmon propagation behavior with strikingly different wavelength dependencies. One method of altering the propagation of the surface plasmon polariton is to dope a nanostructure constructed of a particular metal with another metal. For example, adding small amounts of Ag to Au produces a film with significantly lower losses at short wavelengths. Conversely, the high energy propagation ability of Ag can be compromised through the addition of Au. Another method for propagation control is the use of high optical extinction polymeric coatings or other chemical components, as discussed above. When a high density of plasmon frequency absorbing chromophore is attached to the metal surface, specific propagating energies can be filtered out. Another method of selectively transmitting optical energy is to construct nanostructures that absorb in a narrow portion of the spectral range. In other words, introducing a spectrally broad pulse into the nanostructure and the nanostructure would select a narrow portion of that spectrum for transmission.

E. The following is another illustrative nonlimiting example of a preferred embodiment of the present invention that describes an amplifier. Fluorescently labeling nanostructures should amplify surface plasmon polaritons. By optically pumping laser dyes attached to the nanostructure surfaces, broadband plasmon gain should be possible over a wide range of optical and near infrared frequencies. Because fast energy transfer from the dye to the metal occurs, a small percentage of this energy will be observed as fluorescence, and the rest will be coupled back into the nanostructure at high angles, primarily along the length of the nanostructure. If the surface plasmon polariton are within the correct frequency range as determined by the frequencies over which dyes provide optical gain, the surface plasmon polariton should be coherently amplified. Because the nanostructures necessary for the circuit components are small, co-propagating lasers within the metal nanstructures are unnecessary; one may simply irradiate a large area of the sample in a direction perpendicular to surface plasmon polariton propagation to amplify signals, just as dye amplifiers are used in laser technology. Consequently, irradiation of a chip composed of circuit components constructed with nanostructures in circuit components is needed.

F. An additional aspect of the present invention and all of the embodiments specifically discussed is that separated nanostructures can connect electrically. If a conductive but non-plasmonic structure is placed between the two nanostrucures, plasmon scattering and coupling will still occur, while the ability to piggyback lower frequency electrical signals through the nanostructure will be maintained. This would allow doing both electronic and plasmonic functions on the same nanostructure. Furthermore, the ability to do both electronic and plasmonic functions on the same nanostructure would allow performing electronic and plasmonic computing on the same circuit component. Still further both functions can be performed on a chip, where slower electrical switching could be used for low priority jobs and optical methods would be used for high bandwidth applications.

Figure 4A:
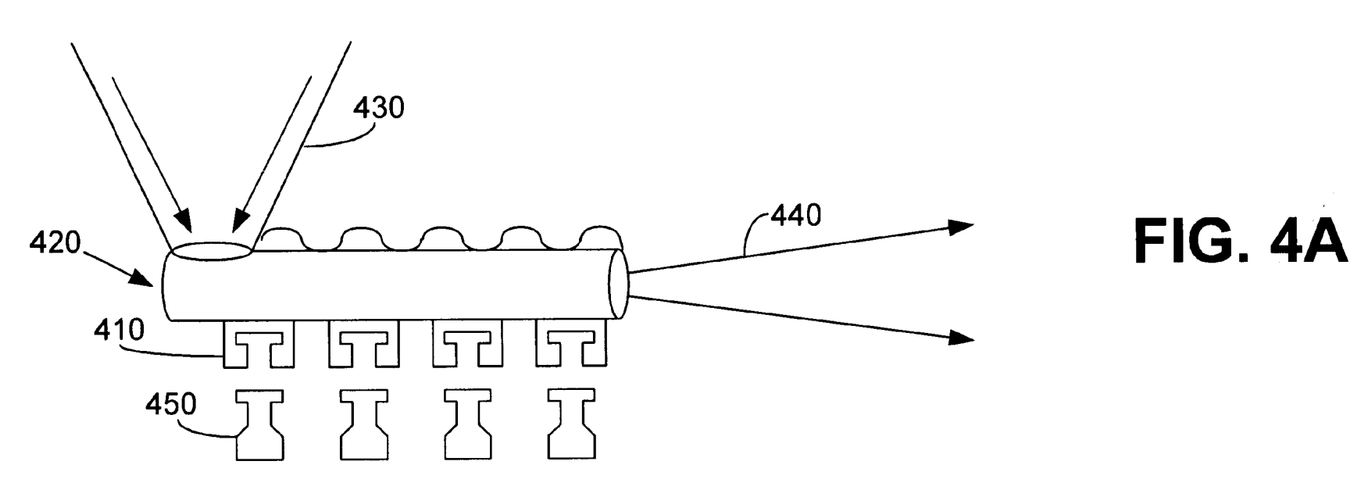
FIGS. 4A and 4B illustrate a nanostructure, similar to the one illustrated in FIG. 1, that has a biological component attached to it.
Figure 4B:
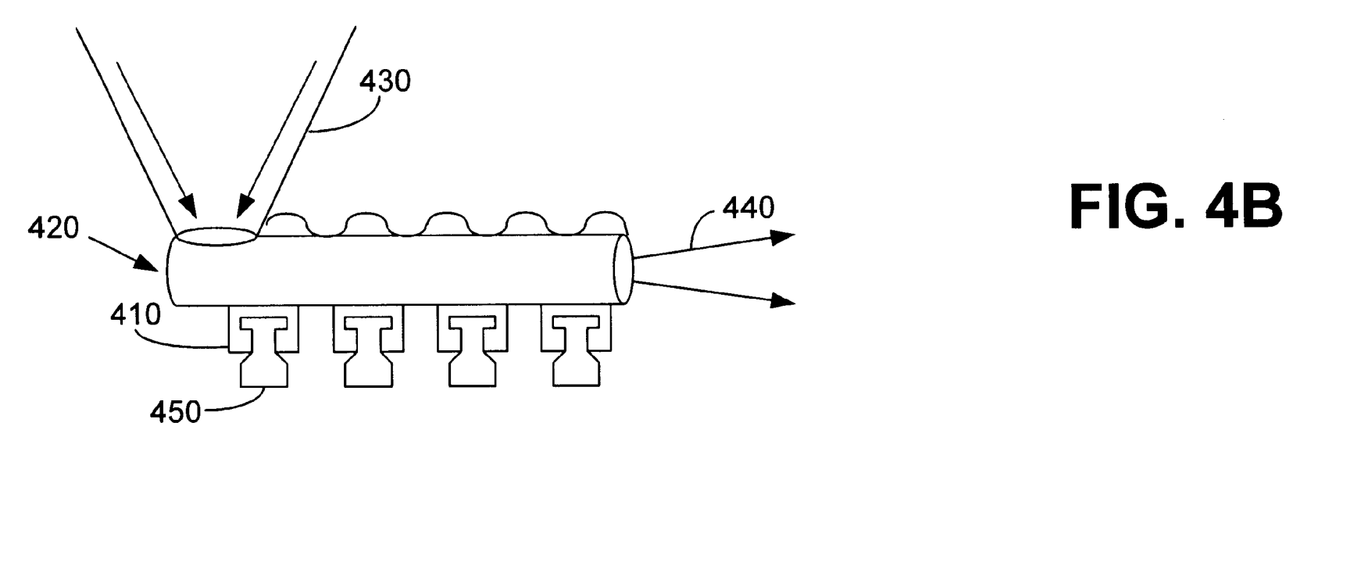

G. The following is another illustrative nonlimiting example of a preferred embodiment of the present invention that describes the detection of biological interactions using nanostructures, as shown in FIGS. 4A and 4B. Detection of biological interactions (e.g., protein-protein, protein-ligand, protein-DNA, DNA-DNA, protein-RNA, protein-lipid, etc.) via nanostructure surface plasmon resonance may be accomplished by a number of possible schemes. Similar to previous preferred embodiments, this embodiment is another example of controlling the emission of the light. The following represent a number of preferred embodiments, although the technology is not intended to be limited as such. In all examples, the nanostructure 420 consists of a large aspect-ratio metal nanostructure 420 with a diameter ranging from approximately 10 nm to approximately 1 micron and a length ranging from approximately 1 micron to >100 microns. As discussed above, the nanostructures 420 can be synthesized via template-directed synthesis, lithography, subcomponent self-assembly or any other appropriate method or combination thereof. Like previous preferred embodiments, the nanostructure 420 can be composed of one or more plasmon-supporting metals (e.g. gold, silver, copper, aluminum) that are segregated into discrete segments, alloyed together, or some combination thereof. In addition, the nanostructure 420 segment can be composed of non-plasmon supporting metals, semiconductors, polymers, or insulating materials, provided the nanostructure is composed of enough of a plasmon-supporting metal to produce the desired results. The biological components 410 can be wild-type (or native) structures, mutated structures, biosynthetic biomolecules, synthetically designed mimics, or any combination thereof. Additionally, the biological components 410 may also be labeled with molecular or particulate structures (e.g., metal nanoparticles, polymer nanoparticles, semiconductor nanoparticles, fluorescent labels, radiolabels, liposomes, vesicles, glass particles, etc) or combinations thereof.

More specifically, nanostructure biosensing can be accomplished by immobilization of one biological component 410 to the nanostructure surface 420, illumination 430 of one end of the nanostructure 420 with monochromatic radiation, and then measuring the intensity of that radiation emitted 440 from the distal nanostructure tip before and after exposure to a liquid biological sample 450, as shown in FIGS. 4A and 4B. Any binding events that occur on the nanostructure 420 surface will cause a change in the local dielectric constant and hence alter the plasmon propagation length. This will be indicated by a change in the emission intensity 450 at the nanostructure 420 distal segment as shown in FIG. 4B. In addition to measuring the emission emanating from the distal tip of the nanostructure 420, the amount of emission along the length of the nanostructure 420 can be measured (not shown). Local increases in dielectric constant can result in localized plasmon scattering, which will result in emission at sites along the nanostructure length other than simply at the distal tip.

H. A further nonlimiting illustrative example would be to use fluorescently labeled biological components or fluorescently labeled nanostructures. The fluorescence intensity of the nanostructure during excitation will change as a function of the amount of immobilized biomolecule due to (a) plasmon intensity as a function of distance from the input end and position of the binding event, and/or (b) fluorescence quenching via energy transfer or electron transfer. Monitoring the intensity and/or spectral distribution of fluorescence will allow for quantitation of the amount of binding that has occurred. The fluorescently labeled biomolecules will be excited by plasmon modes generated. Monitoring of the overall fluorescent intensity will provide for detection and quantitation of binding. In addition, excitation of nanostructures with a spectrally broad source (e.g. polychromatic radiation) will result in differential transmission down the length of the nanostructure of the different wavelengths of light in that source. Binding events will modulate the local dielectric constant and hence the spectral characteristics of the emitted light. Binding events can therefore be detected and quantified by measuring the spectrum and the total intensity emitted both from the nanostructure end and along its length.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

We hereby claim at least the following:

1. A circuit component that functions as a unidirectional conduit comprising a nanostructure having at least one metal, wherein said metal can propagate a first light through said nanostructure and re-emit a second light that has characteristics corresponding to said first light, wherein said nanostructure further comprises a first segment and a second segment, wherein said first segment has a higher potential energy barrier and said second segment has a lower non-zero potential energy barrier and wherein said first segment is a first plasmon supporting metal and said second segment is a second plasmon supporting metal.

2. The circuit component of claim 1, wherein said first light is propagated through said nanostructure using a nanostructure-confined surface plasmon.

3. The circuit component of claim 1, wherein said at least one metal is a plasmon supporting metal.

4. The circuit component of claim 1, wherein said at least one metal is selected from the group consisting of gold, silver, copper, and aluminum.

5. The circuit component of claim 1, wherein said first plasmon supporting metal is gold.

6. The circuit component of claim 1, wherein said second plasmon supporting metal is silver.

7. The circuit component of claim 1 that is designed to function as a transistor.

8. The circuit component of claim 1 that is designed to function as a switch.

9. The circuit component of claim 1 that is designed to function as an amplifier.

10. The circuit component of claim 1 that is designed to function as a filter.

11. The circuit component of claim 1 that can perform electrical functions.

12. The circuit component of claim 1, wherein said nanostructure is coated with a propagation altering material.

13. The circuit component of claim 12, wherein said propagation altering material is a chemical component.

14. The circuit component of claim 12, wherein said propagation altering material is a biological component.

15. The circuit component of claim 14, wherein said biological component alters said reemission of the light.

16. A circuit component comprising a nanostructure having at least one metal, wherein said metal can propagate a first light through said nanostructure and re-emit a second light that has characteristics corresponding to said first light, wherein said nanostructure further comprises a first segment and a second segment, wherein said first segment has a higher potential energy barrier and said second segment has a lower non-zero potential energy barrier.

17. The circuit component of claim 16, wherein said first light is propagated through said nanostructure using a nanostructure-confined surface plasmon.

18. The circuit component of claim 16, wherein said at least one metal is a plasmon supporting metal.

19. The circuit component of claim 16, wherein said at least one metal is selected from the group consisting of gold, silver, copper, and aluminum.

20. The circuit component of claim 16 that is designed to function as a unidirectional conduit.

21. The circuit component of claim 20, wherein said first segment is a first plasmon supporting metal and said second segment is a second plasmon supporting metal.

22. The circuit component of claim 21, wherein said first plasmon supporting metal is gold.

23. The circuit component of claim 21, wherein said second plasmon supporting metal is silver.

24. The circuit component of claim 16 that is designed to function as a transistor.

25. The circuit component of claim 16 that is designed to function as a switch.

26. The circuit component of claim 16 that is designed to function as an amplifier.

27. The circuit component of claim 16 that is designed to function as a filter.

28. The circuit component of claim 16 that can perform electrical functions.

29. The circuit component of claim 16, wherein said nanostructure is coated with a propagation altering material.

30. The circuit component of claim 29, wherein said propagation altering material is a chemical component.

31. The circuit component of claim 29, wherein said propagation altering material is a biological component.

32. The circuit component of claim 29, wherein said biological component alters said reemission of the light.

* * * * *